United States Patent
Kalnes et al.

(10) Patent No.: US 7,414,167 B2
(45) Date of Patent: *Aug. 19, 2008

(54) CONVERSION OF OXYGENATE TO PROPYLENE USING MOVING BED TECHNOLOGY AND A SEPARATE HEAVY OLEFIN INTERCONVERSION STEP

(75) Inventors: Tom N. Kalnes, Des Plaines, IL (US); Timur V. Voskoboynikov, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 188 days.

This patent is subject to a terminal disclaimer.

(21) Appl. No.: 11/036,312

(22) Filed: Jan. 14, 2005

(65) Prior Publication Data

US 2006/0161035 A1    Jul. 20, 2006

(51) Int. Cl.
*C07C 1/00* (2006.01)
(52) U.S. Cl. ...................................... 585/640
(58) Field of Classification Search ........... 585/640
See application file for complete search history.

(56) References Cited

U.S. PATENT DOCUMENTS

| | | | |
|---|---|---|---|
| 4,061,724 A | 12/1977 | Grose et al. | 423/335 |
| 4,073,865 A | 2/1978 | Flanigen et al. | 423/339 |
| 4,269,717 A | 5/1981 | Slovinsky | 210/750 |
| 4,310,440 A | 1/1982 | Wilson et al. | 252/435 |
| 4,387,263 A | 6/1983 | Vogt et al. | 585/640 |
| 4,433,188 A | 2/1984 | Hoelderich et al. | 585/640 |
| 4,440,871 A | 4/1984 | Lok et al. | 502/214 |
| 4,498,973 A | 2/1985 | Sikonia et al. | 208/63 |
| 4,527,001 A | 7/1985 | Kaiser | 585/643 |

(Continued)

FOREIGN PATENT DOCUMENTS

EP    0 448 000 B1    5/1994

(Continued)

OTHER PUBLICATIONS

Rothaemel et al., "Demonstrating the New Methanol to Propylene (MTP) Process", Mar. 2003, ERTC Petrochemical Conference, Paris, France.

(Continued)

*Primary Examiner*—Glenn Caldarola
*Assistant Examiner*—In Suk Bullock
(74) *Attorney, Agent, or Firm*—Mark Goldberg

(57) ABSTRACT

The average propylene cycle yield of an oxygenate to propylene (OTP) process using a dual-function oxygenate conversion catalyst is substantially enhanced by the use of a combination of: 1) moving bed reactor technology in the catalytic OTP reaction step in lieu of the fixed bed technology of the prior art; 2) a separate heavy olefin interconversion step using moving bed technology and operating at an inlet temperature at least 15° C. higher than the maximum temperature utilized in the OTP reaction step; 3) $C_2$ olefin recycle to the OTP reaction step; and 4) a catalyst on-stream cycle time of 700 hours or less. These provisions hold the build-up of coke deposits on the catalyst to a level which does not substantially degrade dual-function catalyst activity, oxygenate conversion and propylene selectivity, thereby enabling maintenance of average propylene cycle yield for each cycle near or at essentially start-of-cycle levels.

27 Claims, 1 Drawing Sheet

U.S. PATENT DOCUMENTS

| | | | |
|---|---|---|---|
| 4,554,143 A | 11/1985 | Messina et al. | 423/306 |
| 4,579,999 A | 4/1986 | Gould et al. | 585/312 |
| 4,587,373 A | 5/1986 | Hsia | 585/639 |
| 4,629,717 A | 12/1986 | Chao | 502/208 |
| 4,677,243 A | 6/1987 | Kaiser | 585/638 |
| 4,752,651 A | 6/1988 | Kaiser | 585/640 |
| 4,793,984 A | 12/1988 | Lok et al. | 423/306 |
| 4,853,197 A | 8/1989 | Wilson et al. | 423/306 |
| 4,873,390 A | 10/1989 | Lewis et al. | 585/638 |
| 5,095,163 A | 3/1992 | Barger | 585/640 |
| 5,126,308 A | 6/1992 | Barger et al. | 502/214 |
| 5,157,181 A | 10/1992 | Stine et al. | 585/329 |
| 5,191,141 A | 3/1993 | Barger et al. | 585/640 |
| 6,437,208 B1 * | 8/2002 | Kuechler et al. | 585/640 |
| 6,455,749 B1 * | 9/2002 | Vaughn | 585/640 |
| 2003/0139635 A1 | 7/2003 | Hack et al. | 585/609 |
| 2004/0102667 A1 | 5/2004 | Vora et al. | 585/324 |

FOREIGN PATENT DOCUMENTS

| | | |
|---|---|---|
| EP | 1 025 068 B1 | 1/2003 |
| GB | 2 171 718 A | 9/1986 |

OTHER PUBLICATIONS

Paper "Insights in Gas to Propylene, GTP®/MTP® Technology" by Dr. Waldemar Liebner, Lurgi AG, Frankfurt am Main; Germany, presented at Propylene Trade & Derivatives Markets, Singapore, Oct. 24-25, 2005.

* cited by examiner

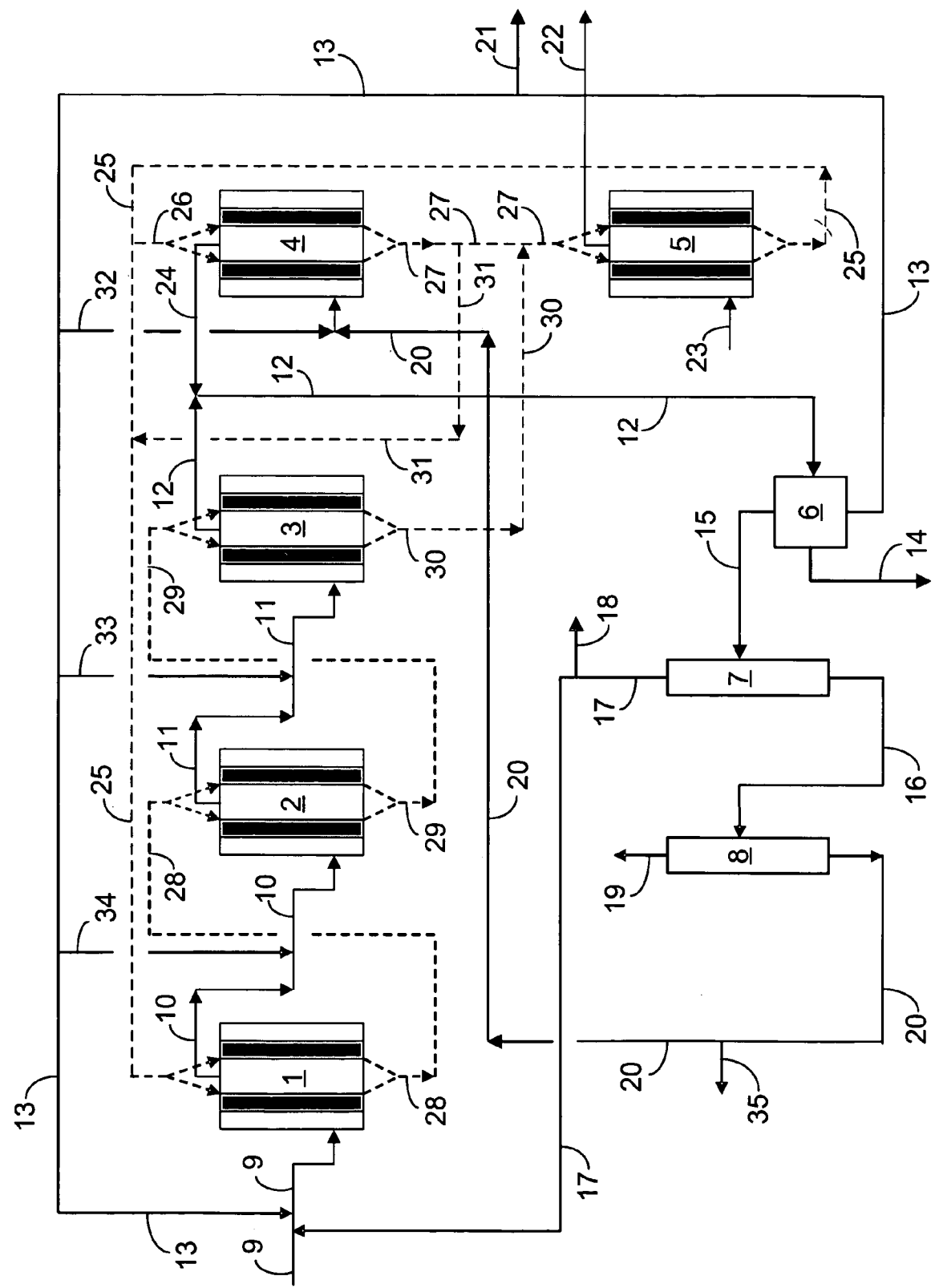

US 7,414,167 B2

CONVERSION OF OXYGENATE TO PROPYLENE USING MOVING BED TECHNOLOGY AND A SEPARATE HEAVY OLEFIN INTERCONVERSION STEP

FIELD OF THE INVENTION

The present invention relates generally to the use of a separate heavy olefin interconversion step using a dual-function catalyst and moving bed technology in a continuous process for conversion of an oxygenate to propylene (OTP) where the oxygenate conversion step also uses a dual-function catalyst, moving bed technology and operates at relatively low temperatures, compared to the heavy olefin interconversion step, preferably with a steam diluent. Use of a separate heavy olefin interconversion step operating with a moving bed reactor system and with a relatively higher conversion temperature enables tight control of the maximum temperatures experienced in the oxygenate conversion step which in turn helps control catalyst deactivation not only during an on-stream cycle but also on a cycle-to-cycle basis. This type of two reaction zones operation enables the holding of coke level on the dual-function catalyst used in the oxygenate conversion step to a value that does not significantly degrade the activity and propylene selectivity of this catalyst for an extended period relative to the results reported for the fixed bed operation of the prior art. These provisions in turn lead to a sharp improvement in the average propylene cycle yield achievable by this modified OTP process not only over its initial on-stream catalyst cycle time but also over subsequent cycles relative to the average propylene cycle yield that is achievable by a prior art process that uses fixed bed reactor technology and an oxygenate conversion step which performs both the OTP reactions and the heavy olefin interconversion reactions simultaneously. The present invention more specifically relates to an improved catalytic oxygenate to propylene process that uses a combination of a dual reaction zone system, with interconversion of heavy olefin by-products performed exclusively in the second higher temperature reaction zone, and of moving bed technology to hold average cycle catalytic activity and propylene selectivity nearer to the start of the initial cycle levels during the entire on-stream operating time, thereby sharply improving the average propylene yield achieved by this modified reaction system over its life cycle relative to that achievable with the same or similar dual-function catalyst in an OTP process of the prior art that uses a single reaction zone to effect both OTP reactions and heavy olefins interconversion. The key to the present invention involves recognition that propylene yield achievable over dual-function OTP catalyst systems known in the art operating preferably with a steam diluent at relatively high temperatures is very sensitive to deactivation not only by coke deposition but also by hydrothermal dealumination (accelerated by exposure to high temperatures in the presence of steam which temperatures are needed both in the OTP reaction step and in the OTP catalyst regeneration step to compensate for the activity loss caused by this excessive coke deposition) and recognition that use of a separate heavy olefin interconversion zone enables lower temperature operation of the OTP reaction zone, thereby lowering deactivation and enhancing propylene yield. Stated another way, the key to the present invention is the fact that propylene yield in an OTP catalytic process operating with a dual-function catalyst system and in a moving bed reactor mode can be continuously maintained at or near start-of-run levels if the reaction system is modified in accordance with the present invention to enhance catalyst stability.

BACKGROUND OF THE INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. In other words, the holy grail of the R & D personnel assigned to work in this area is to find a way to effectively and selectively use alternative feedstocks for this light olefin production application, thereby lessening dependence of the petrochemical industry on petroleum feedstocks. A great deal of the prior art's attention has been focused on the possibility of using hydrocarbon oxygenates and more specifically methanol or dimethylether (DME) as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst in a steam reforming step followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products in order to make an oxygenate to olefin (OTO) process. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. A review of the prior art has revealed essentially two major techniques that are discussed for conversion of methanol to light olefins (MTO). The first of these MTO processes is based on early German and American work with a catalytic conversion zone containing a zeolitic type of catalyst system. Representative of the early German work is U.S. Pat. No. 4,387,263 which was filed in May of 1982 in the U.S. without a claim for German priority. This '263 patent reports on a series of experiments with methanol conversion techniques using a ZSM-5 type of catalyst system wherein the problem of DME by-product recycle is a major focus of the technology disclosed. Although good yields of ethylene and propylene were reported in this '263 patent, they unfortunately were accompanied by substantial formation of higher aliphatic and aromatic hydrocarbons which the patentees speculated might be useful as an engine fuel and specifically as a gasoline-type of material. In order to limit the amount of this heavier material that is produced, the patentees of the '263 patent propose to limit conversion to less than 80% of the methanol charged to the MTO conversion step. This operation at lower conversion levels necessitated a critical assessment of means for recovering and recycling not only unreacted methanol but also substantial amounts of a DME intermediate product. The focus then of the '263 patent invention was therefore on a DME and methanol scrubbing step utilizing a water solvent in order to efficiently and effectively recapture the light olefin value of the unreacted methanol and of the intermediate reactant DME.

This early MTO work with a zeolitic catalyst system was then followed up by the Mobil Oil Company who also investigated the use of a zeolitic catalyst system like ZSM-5 for purposes of making light olefins. U.S. Pat. No. 4,587,373 is representative of Mobil's early work and it acknowledged and distinguished the German contribution to this zeolitic catalyst based MTO route to light olefins. The inventor of the '373 patent made two significant contributions to this zeolitic MTO route the first of which involved recognition that a commercial plant would have to operate at pressure substantially above the preferred range that the German workers in this field had suggested in order to make the commercial equipment of reasonable size when commercial mass flow rates are desired. The '373 patent recognized that as you move to higher pressure for the zeolitic MTO route in order to control the size of the equipment needed for commercial plant there is a substantial additional loss of DME that was not considered in the German work. This additional loss is caused by dissolution of substantial quantities of DME in the heavy hydrocarbon oil by-product recovered from the liquid hydrocarbon stream withdrawn from the primary separator. The other significant contribution of the '373 patent is manifest from inspection of the flow scheme presented in FIG. 2 which prominently features a portion of the methanol feed being diverted to the DME absorption zone in order to take advantage of the fact that there exists a high affinity between methanol and DME thereby downsizing the size of the scrubbing zone required relative to the scrubbing zone utilizing plain water that was suggested by the earlier German work.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. No. 5,095,163; U.S. Pat. No. 5,126,308 and U.S. Pat. No. 5,191,141 are representative. This second approach to MTO conversion technology was primarily based on using a catalyst system comprising a non-zeolitic molecular sieve, generally a metal aluminophosphate (ELAPO) and more specifically a silicoaluminophosphate molecular sieve (SAPO), with a strong preference for a SAPO species that is known as SAPO-34. This SAPO-34 material was found to have a very high selectivity for light olefins with a methanol feedstock and consequently very low selectivity for the undesired corresponding light paraffins and the heavier materials. This ELAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke made in the MTO conversion zone relative to that experienced with the zeolitic catalyst system.

The classical OTO technology produces a mixture of light olefins primarily ethylene and propylene along with various higher boiling olefins. Although the classical OTO process technology possesses the capability of shifting the major olefin product recovered therefrom from ethylene to propylene by various adjustments of conditions maintained in the reaction zone, the art has long sought an oxygenate to propylene (OTP) technology that would provide better yields of propylene relative to the classical OTO technology. The driving force for this shift in emphasis towards propylene is the growth rate of the propylene market versus the growth rate of the ethylene market. The existing sources of propylene production in the marketplace are primarily based on conventional steam cracking of naphtha, LPG streams, propane streams and the like. Another major existing source of propylene is of course the olefins that are produced in a fluid catalytic cracking (FCC) hydrocarbon conversion process in the modern day refinery. Because the basic raw material used in an OTO process is derived from natural gas which is widely available particularly in remote areas of the world but unfortunately markets for this gas are typically not conveniently available near the location of the remote gas fields. These remote gas fields tend to be quite large and because of the relatively well-developed technology for converting natural gas to methanol and other oxygenates are viewed by those skilled in this art as being the next logical source of large-scale propylene production provided a commercially acceptable OTP process can be established which possesses intrinsic high selectivity for the desired propylene product.

Workers at Lurgi Oel Gas Chemie GmbH have recently announced a new fixed bed methanol to propylene (MTP) process which according to Lurgi offers the potential to satisfy the arts' thirst for a propylene selective OTO type of process. It appears that the basic flow scheme and technical details of the Lurgi process offering in this field have been relatively recently disclosed in a U.S. application publication, Publication No. US2003/0139635A1 which was published on Jul. 24, 2003 and describes a process for selectively producing propylene from a feedstock which comprises methanol and/or DME. Analysis of the two figures attached to this patent publication make it clear that Lurgi contemplates a reactor flow configuration for the oxygenate to propylene (OTP) synthesis portion of its flow scheme wherein three reactors are utilized with a steam diluent and fixed beds of oxygenate conversion catalysts in a parallel flow arrangement with respect to the oxygenate feed. The reactors are connected in a serial flow arrangement with respect to the effluents of the first reactor and the second reactor. The dual function OTP catalyst system taught as being useful in this flow scheme is rather narrowly defined in paragraph [0005] of this patent publication as a pentasil-type (i.e. ZSM-5 or ZSM-11 type) having an alkali content less than 380 ppm and a zinc oxide content of less than 0.1 wt-% coupled with a restriction on cadmium oxide content of the same amount. The teachings with respect to this catalyst are derived from a European patent, EP-B-0448000, filed by Sud Chemie and Lurgi claiming priority from an original German application that was filed in March of 1990. Thus the catalyst contemplated for use in Lurgi's flow scheme is well known to those skilled in this art. According to Lurgi's marketing presentation, the on-stream portion of the process cycle for this MTP process is expected to be 500 to 700 hours before in situ regeneration becomes necessary. (See Rothaemel et al. "Demonstrating the New Methanol to Propylene (MTP) Process" presented to the ERTC Petrochemical Conference in March of 2003 at Paris, France). The activity-stability of the MTP catalyst in this Lurgi presentation show a significant drop in conversion activity over the first five cycles with each cycle being terminated after the oxygenate conversion level drops to about 94% to 95% of the oxygenate feed. No mention is made in this paper of a corresponding drop in propylene yield and instead the average once-through propylene selectivity over the on-stream cycle is discussed and a table presented showing that it ranges from 30% to 40% of the converted products with a number between 68% to 71% presented as an estimate of the average cycle yield for propylene over the 500 to 700 hour cycle length expected to be achieved by this flow scheme with full by-product olefin recycle. Lurgi also contemplates that at the end of the cycle when the conversion has dropped to a level of about 94% of the equivalent in the feed that the reactors will be shut down and the catalyst regenerated in situ using an air/nitrogen mixture to burn off the detrimental coke deposits.

Although Lurgi does not state exactly what countermeasures it takes during its process cycle in order to compensate for the falloff in activity of its dual-function MTP catalyst due to coke deposition, we believe that Lurgi undoubtedly follows the conventional procedure for compensating for activity decay in a catalytic operation involving an increase in the average reactor temperature in order to attempt to hold conversion in the targeted range of greater than 94% of the oxygenate charge. Under these circumstances it is our considered opinion based on experimental results with similar dual-function catalysts and similar feeds that the falloff of propylene yield over the cycle is accelerated by the coke deposition, by the use of a steam diluent and by the attempt to take countermeasures to compensate and we believe that the yield falloff will be greater than the activity falloff by a factor of 1.25 to 3.5 or more depending somewhat on the exact composition of the catalyst used, its hydrothermal stability and the operating condition changes that are made during the cycle to attempt to compensate for the falloff in activity.

ExxonMobil in EP-B-1025068 has proposed a two reaction zone solution to the problem of effectively converting an oxygenate feed and a by-product fraction containing $C_4^+$ hydrocarbons to ethylene and propylene. According to this teaching the advantages of a two reaction zone system include independent selection of catalyst and conversion conditions for each zone. This '068 patent in fact teaches the use of non-zeolitic molecular sieve catalyst such as the preferred SAPO-34 for the oxygenate to light olefin reaction zone and either a non-zeolitic molecular sieve catalyst or a zeolitic catalyst such as the preferred ZSM-5 material for the auxiliary reaction zone which operates to convert the $C_4^+$ by-product fraction to the desired light olefin (i.e. $C_2$ and $C_3$ olefins). In Example III of this '068 patent evidence is presented showing that a relatively high temperature of about 600° C. provides superior conversion and light olefin selectivity with a SAPO-34 catalyst in the second or auxiliary reaction zone. This '068 patent does not in fact teach moving bed technology for either reaction zone preferring a circulating fluid bed or a riser reaction for the first reaction zone (see [0030]) and a fluid bed or a fixed bed or a fixed tube reactor for the second reaction zone (see [0031]). The '068 patent also does not teach a propylene selective process but one focused on making both $C_2$ and $C_3$ olefins, nor does it teach any $C_2$ olefin product recycle to its first reaction zone for conversion to additional quantities of propylene.

The problem addressed by the present invention is then to modify this Lurgi OTP or MTP process of the prior art which we believe uses a dual-function catalyst system that suffers from hydrothermal instability and which uses a $C_4^+$ by-product recycle to the OTP or MTP reaction zone, in order to enhance its average propylene yield not only over its on-stream cycle time but also on a cycle-to-cycle basis and thereby diminish the requirement for recycle of olefin products other than propylene in order to compensate for lower propylene yield. We have now discerned that overall propylene yield is a function not only of reaction conditions and of average coke level deposited on the OTP conversion catalyst during the on-stream portion of each of the process cycles but also of the hydrothermal stability of the dual-function catalyst system utilized when it is exposed to steam at relatively high conversion temperatures necessitated by recycle of the relatively refractory $C_4^+$ by-product material to the OTP reaction zone. We have discovered furthermore that the use of moving bed technology in conjunction with a two reaction zone system can be used to shift the conversion of the relatively refractory $C_4^+$ by-product material to a separate moving bed reaction zone, thereby controlling the temperature required in the OTP reaction step to a lower range. Put another way we have now found that average propylene yield in an OTP process operated in a moving bed mode can be significantly enhanced if a dual reaction zone system is used therein with the second zone operating at an inlet conversion temperature at least 15° C. higher than the maximum temperature used in the OTP reaction step and using a feed thereto the $C_4^+$ olefin by-product material from the OTP reaction step, thereby enabling the OTP reaction step to run under less severe conditions which in turn suppresses hydrothermal deactivation of the dual-function catalyst used therein.

The instant application is a companion case to UOP's prior filed cases on the application of moving bed technology to an OTP process. The first was filed Jun. 25, 2004 as application Ser. No. 10/876,394; the second filed Sep. 16, 2004 as application Ser. No. 10/943,833; the third filed Sep. 21, 2004 as application Ser. No. 10/946,605 all of the teachings of which are incorporated herein by reference and the fourth was filed on Nov. 12, 2004 as application Ser. No 10/988,136.

SUMMARY OF THE INVENTION

The primary objective of the present invention is to provide a realistic and technically feasible solution to the problem of propylene yield loss during the on-stream cycle as well as the cycle-to-cycle loss caused by recycle of the $C_4^+$ by-product material to the fixed bed OTP conversion step of the prior art when operated with a steam diluent and with a steam sensitive dual-function catalyst system. A secondary objective is to improve the economics of this prior art OTP process by using moving bed technology and a dual reaction zone system to help control coke-induced deactivation and hydrothermal deactivation of the dual-function catalyst used therein in order to maintain oxygenate conversion and propylene yield at higher levels relative to the prior art. Another object of the present invention is to avoid severe reaction conditions in the OTP conversion step that can cause hydrothermal deactivation of the dual-function catalyst utilized in this process. A more general objective is to combine moving bed technology and a dual reaction zone system, with the first reaction zone focused on the OTP reactions and the second reaction zone exclusively performing the $C_4^+$ olefin by-product to propylene interconversion reactions, in order to provide a more efficient OTP process.

In one embodiment the instant invention is a continuous process for the selective conversion of an oxygenate feed to propylene utilizing molecular sieve-based dual-function catalyst technology, dual reaction zone technology and moving bed technology to maintain catalyst performance near or at essentially start-of-cycle levels in the initial cycle-as well as in subsequent cycles, thereby enhancing the average cycle yield of propylene and minimizing oxygenate breakthrough into the product stream. In the first step of the process an oxygenate feed and a first diluent in an amount corresponding to about 0.1:1 to 12:1 moles of diluent per mole of oxygenate are contacted with particles of a first dual-function catalyst, containing a catalytically effective amount of a molecular sieve having the ability to convert oxygenates to propylene and to interconvert $C_2$ and $C_4^+$ olefins to $C_3$ olefins, in a first reaction zone containing at least one moving bed reactor which is operated at oxygenate conversion conditions effective to selectively convert oxygenate to propylene and to convert any ethylene recycled thereto to propylene. A first effluent stream is then withdrawn from the first reaction zone and found to contain major amounts of a $C_3$ olefin product and a water by-product; lesser amounts of a $C_2$ olefin, $C_4^+$ olefins, $C_1$ to $C_4^+$ saturated hydrocarbons and aromatic hydrocarbons; and minor amounts of unreacted oxygenate, by-product oxygenates and highly unsaturated hydrocarbons (such as dienes and acetylenic hydrocarbons). In the second step this first effluent stream is passed to a first separation zone and therein cooled and separated into a vaporous fraction rich in $C_3$ olefins, a water fraction containing unreacted oxygenate and by-product oxygenates and a liquid hydrocarbon fraction containing heavier olefins, heavier saturated hydrocarbons and minor amounts of highly unsaturated hydrocarbons and aromatic hydrocarbons. At least a portion of the water fraction recovered in this first separation step is in the next step recycled to the oxygenate conversion step to provide at least a portion of the first diluent used therein. The vaporous fraction recovered in this first separation step is further separated in a second separating step into a $C_2$ olefin-rich fraction, a $C_3$ olefin-rich product fraction and a first $C_4^+$ olefin-rich fraction containing minor amounts of highly unsaturated hydrocarbons. At least a portion of the $C_2$ olefin-rich fraction is recycled to the first reaction zone. The $C_3$ olefin-rich product fraction is then recovered as a principal product stream from the present process. At least a portion of the $C_4^+$ olefins contained in the first $C_4^+$ olefin-rich fraction is either charged directly to a second reaction zone containing particles of a second dual-function catalyst or to an optional selective hydrogen treatment step with at least a portion of the effluent therefrom being subsequently charged to the second reaction zone. This second reaction zone contains at least one moving bed reactor containing particles of the second dual-function catalyst and is operated at heavy olefin interconversion conditions, including an inlet temperature at least 15° C. higher than the maximum temperature used in the first reaction zone, effective to convert a substantial portion of the heavy olefins charged thereto to propylene and to produce a second effluent stream containing major amounts of propylene. The optional selective hydrogen treating step is designed to selectively convert highly unsaturated compounds contained in this $C_4^+$ olefin-rich stream into the corresponding olefin, thereby eliminating coke precursors from the heavy olefin interconversion step. This optional catalytic hydrotreating step is performed by contacting at least a portion of this first $C_4^+$ olefin-rich stream and hydrogen with a metal-containing hydrogenation catalyst at selective hydrogenation conditions effective to convert highly unsaturated hydrocarbons contained therein to the corresponding olefin and to produce a selectively hydrotreated $C_4^+$ olefin-rich fraction. At least a portion of this last fraction is then charged as previously indicated to the second reaction zone in order to interconvert these heavier olefinic materials into additional quantities of the desired propylene product. The second effluent stream is then withdrawn from the second reaction zone and at least a portion thereof is charged to the first separating zone and further separated therein as specified hereinbefore. Coke-containing particles of the first dual-function catalyst are then withdrawn from the first reaction zone and charged to a first moving bed regeneration zone wherein they are oxidatively regenerated and at least a portion of the resulting regenerated catalyst particles are passed back to the first reaction zone thereby enabling continuous operation of the first reaction zone. Coke-containing particles of the second dual-function catalyst are also withdrawn from the second reaction zone and charged to a second moving bed regeneration zone and at least a portion of the resulting regenerated catalyst particles are passed back to the second reaction zone, thereby enabling continuous operation of the second reaction zone.

A second embodiment involves a continuous process for the selective conversion of an oxygenate feed to propylene as described in the first embodiment wherein the first and second dual-function catalysts contain a zeolitic molecular sieve having a structure corresponding to ZSM-5 or ZSM-11 or contain an ELAPO molecular sieve having a structure corresponding to SAPO-34 or a mixture of these materials.

Another embodiment comprises a continuous process for selective conversion of an oxygenate feed to propylene as described above in the first embodiment wherein the first reaction zone contains at least 3 moving bed reactors which are connected in a serial flow or parallel flow configuration with respect to oxygenate feed and in a serial flow configuration with respect to the stream of catalyst particles that passes therethrough.

A highly preferred embodiment of the present invention comprises a continuous process for the selective conversion of an oxygenate feed to propylene as described above in the first embodiment wherein the oxygenate feed contains methanol or dimethylether or a mixture thereof. In this embodiment the instant process is referred to herein as a methanol to propylene embodiment (MTP).

A high propylene yield embodiment of the instant process involves the continuous process for selective conversion of an oxygenate feed to propylene as described in any of the previous embodiments wherein the liquid hydrocarbon fraction recovered in the first separation step is further separated into a second $C_4^+$ olefin-rich fraction and a naphtha product fraction and at least a portion of the resulting second $C_4^+$ olefin-rich fraction is charged either directly to the second reaction zone or to the optional selective hydrogen treatment step and thereafter the resulting hydrogen-treated product is charged to the second reaction zone in order to interconvert these heavier olefins into propylene.

Other objects, embodiments, advantages and features of the present invention will be clear to somebody of ordinary skill in the chemical engineering art from a detailed examination of the following description of the invention as well as the information contained in the attached drawing.

BRIEF DESCRIPTION OF THE DRAWING

The FIGURE is a process flow diagram of a highly preferred embodiment of the present invention which portrays the essential interconnections and interrelationships between the various operating zones preferably utilized to selectively and continuously convert an oxygenate feed to propylene wherein a first reaction zone containing at least three moving bed reactors loaded with a preferred dual-function catalyst system is used to perform the OTP conversion and ethylene interconversion step and a second reaction zone containing one moving bed reactor loaded with the same dual-function catalyst is used to perform the heavy olefin interconversion step. In this drawing, lines utilized for circulation of reactants and products are drawn as solid lines whereas lines exclusively used for circulation of OTP catalyst particles are drawn as dotted lines.

TERMS AND CONDITIONS DEFINITIONS

The following terms and conditions are used in the present specification with the following meanings: (1) A "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) An "overhead" stream means the net overhead recovered from the specified zone after recycle of any portion to the zone for reflux or any other reason. (3) A "bottom" stream means the net bottom stream from the specified zone obtained after recycle of any portion for purposes of reheating and/or reboiling and/or after any phase separation. (4) A line or reactor is "blocked-off" when it contains one or more valves that are set to a position that prevents flow through the line or reactor. (5) Presence of necessary compressors and/or pumps is understood when flow is shown from a zone of relatively low pressure to a zone of higher pressure. (6) Presence of necessary heating and/or cooling means is implied when flow is shown between zones operating at different temperatures. (7) An ingredient is "lifted" or "stripped" when it is concentrated in the overhead stream withdrawn from the specified zone. (8) A "vapor" stream means a stream containing one or more components in the gaseous state. (9) The term "light olefins" means ethylene, propylene and mixtures thereof. (10) The term "heavy olefin" means an olefin having a molecular weight greater than propylene. (11) The expression "OTP" process means a process for converting an oxygenate to propylene and in a preferred embodiment when the oxygenate is methanol the OTP process is referred to as an "MTP" process herein. (12) The term "oxygenate" means an oxygen-substituted aliphatic hydrocarbon containing 1 to 10 carbon atoms. (13) The term "catalyst on-stream cycle time" means the length of time the catalyst particle is exposed to feed or by-products of the feed at conversion conditions before being withdrawn from the reaction zone for regeneration in a separate regeneration zone (moving bed system) or the reaction zone is blocked off for in situ regeneration (fixed bed system). (14) The term "average propylene cycle yield" means the total propylene yield during the catalyst on-stream cycle time divided by the total amount of oxygenate feed converted during the catalyst on-stream cycle time. (15) The term "dual-functional" means that the OTP catalyst catalyzes both the OTP reactions and the olefin interconversion reactions necessary to convert $C_2$ and $C_4^+$ olefins to propylene. (16) The term "highly unsaturated hydrocarbon" means a hydrocarbon which contains two or more double bonds or a triple bond in its structure. (17) The term "moving bed technology" means that particles of the catalyst move through the reaction zone or the regeneration zone in a compact, non-fluidized bed driven primarily by the action of gravity.

DETAILED DESCRIPTION OF THE INVENTION

In the instant OTP process the feedstream comprises one or more oxygenates. The term "oxygenate" is employed herein to include aliphatic alcohols, ethers, and carbonyl compounds (e.g. aldehydes, ketones, carboxylic acids, and the like) and mixtures of these materials. The oxygenate feedstock preferably contains at least one oxygen atom and about 1 to 10 carbon atoms, and more preferably contains from about 1 to 4 carbon atoms. Suitable oxygenates include lower straight or branched chain alcohols, and their unsaturated counterparts. Representatives of suitable oxygenate compounds include methanol, dimethyl ether (DME), ethanol, diethyl ether, methylether, formaldehyde, dimethyl ketone, acetic acid, and mixtures thereof. A preferred feedstream contains methanol or dimethylether and mixtures thereof.

In the OTP conversion step of the present invention, the oxygenate feed is catalytically and selectively converted in a first reaction zone to propylene and by-product hydrocarbons containing aliphatic moieties such as—but not limited to—methane, ethane, ethylene, propane, butylene, butane and limited amounts of other higher carbon number aliphatics by contacting the feedstock with a dual-function OTP catalyst at effective OTP conditions. This OTP conversion step also forms minor amounts of highly unsaturated hydrocarbons, such as dienes and acetylenic hydrocarbons, and aromatic hydrocarbons. A diluent is not absolutely required but is a useful option to maintain the selectivity of the OTP catalyst to produce light olefins, particularly propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the diluent from the product requires only a simple condensation step to separate water from the light olefin products.

A diluent is thus preferably used in the first reaction zone in order to control partial pressure of the oxygenate reactant to provide a heat sink for the net exothermic reactions occurring herein and to shift the overall reaction selectivity towards propylene. Suitable diluents for use in the first reaction zone include helium, argon, nitrogen, carbon monoxide, carbon dioxide, hydrogen, water, $C_1$ through $C_5$ paraffins, aromatic hydrocarbons and mixtures of these materials. Preferred diluents are steam, methane, an aromatic compound, and mixtures thereof. The best diluents are relatively inert at the conditions maintained in the first reaction zone. An especially preferred diluent for use in the first reaction zone is steam since it is relatively easily recovered from the effluent stream therefrom utilizing condensation techniques. The amount of diluent used will be selected from the range of 0.1:1 to 12:1 and more typically from about 0.1:1 to 5:1 moles of diluent per mole of oxygenate in order to lower the partial pressure of the oxygenates to a level which favors production of propylene. All embodiments of the present invention envision recycling to this first reaction zone of at least a portion of an ethylene-rich by-product stream that contains significant amounts of ethylene and minor amounts of $C_2$ saturated hydrocarbons. This $C_2$ olefin recycle stream will thus furnish saturated $C_2$ hydrocarbon diluent to the first reaction zone and therefore the amount of diluent that must be added to the first reaction zone in order to achieve the target diluent to oxygenate mole ratio will diminish once the first reaction zone is started up and $C_2$ by-product recycle initiated. In the most preferred case where steam is used as the diluent the amount of steam charged to the first reaction zone during startup will diminish in proportion to the amount of saturated hydrocarbons and other inert materials that are recycled to this reaction zone.

An essential feature of the present invention is the use of a separate (or second) reaction zone for interconversion of the heavy olefin by-product stream, (i.e. the $C_4^+$ stream) recovered from the effluent from the OTP conversion step. In the prior art OTP process from Lurgi both the C2 olefin by-product stream and the $C_4^+$ olefin by-product were charged to the OTP conversion step. The present invention in contrast only charges the $C_2$ olefin by-product stream to the OTP conversion step and uses a separate second reaction zone to handle the interconversion of heavy olefin by-product stream into additional amounts of propylene. The principal reason for this strategy is our finding that this heavy olefin by-product is refractory or relatively difficult to interconvert into propylene as compared to the OTP reaction and the ethylene interconversion reaction. The presence of this stream in the OTP reaction step therefore necessitates a significantly higher conversion temperature in the OTP conversion step in order to get acceptable interconversion thereof to propylene than is necessary in the absence of this heavy olefin by-product stream. Higher conversion temperatures in the presence of a steam diluent in turn accelerate dual-function catalyst deactivation and lead to a significant loss in propylene yield for the prior art process relative to the instant process.

The conversion conditions used in the first reaction zone in accordance with the present invention are carefully chosen to favor the production of propylene from the oxygenate charged in the feed. The art has already established an oxygenate conversion temperature range of about 350° to 600° C. as being effective for the conversion of oxygenate over the known oxygenate conversion catalyst. The lower portion of this oxygenate conversion temperature range with certain catalysts is known to favor the production of propylene with the upper portion favoring the production of ethylene at the expense of propylene. Preferred inlet temperatures to the first reaction zone are therefore in the range of 350° to 500° C., more preferably in the range of about 375° to 500° C. and most preferably in the range of 375° to 475° C. The temperature increase across each of the OTP reactors in the first reaction zone is preferably held to a number which is in the range of 10° to 80° C. in order to minimize hydrothermal deactivation of the catalyst and to avoid the acceleration of coke deposition on the catalyst that is experienced when the temperature of the tail end of the individual OTP reactors is allowed to build to levels beyond those contemplated by the present invention. There are numerous methods known to those of ordinary skill in this art for controlling the temperature increase in a reaction zone and most of them involve utilization of multiple beds of catalyst in separate reactors with inner-bed or inter-bed cooling utilizing appropriate heat exchange means and/or addition of relatively cool amounts of recycle streams, or portions of the oxygenate feed and/or the diluents that is utilized in the zone. In the particular case contemplated by the present invention involving the use of ethylene by-product recycle with consequential $C_2$ olefin interconversion reactions, which are known to be highly exothermic, because of the involved dimerization reaction, careful attention to this temperature increase control is extremely important. As will be shown by reference to the attached drawing, the preferred mode of operation of the first reaction zone is to use at least 3 moving bed reactors with interbed quench achieved at least in part by the use of relatively cool recycle streams to provide additional quantities of reactants and diluent.

The conversion conditions employed in the second reaction zone are carefully chosen in light of our finding discussed earlier to emphasize the selective conversion of the heavy olefin by-product stream, that in accordance with the present invention is charged to this zone, to propylene. Since the heavy olefin interconversion reactions that are performed in this zone are mildly endothermic, the inlet temperature into this second zone is the key variable since the temperature delta across this zone is negative. The inlet temperature to this second zone is set at a relatively high value reference to the maximum or peak temperature experienced in the first reaction zone (which is typically at or near the outlet of the reactors in this zone since balance of the OTP reactions and $C_2$ olefin interconversion reactions are strongly exothermic). In fact a feature of the present invention is that the inlet temperature into the second reaction zone (or into each reactor if multiple reactors are utilized) is at least 15° C. higher than the maximum temperature reached in the first reaction zone. Best results are obtained when this inlet temperature is set so that it is 15° to 25° C. or more higher than the maximum temperature experienced in the first reaction zone.

A diluent is preferably used in this second reaction zone in order to control partial pressure of the heavy olefin reactant used therein and to provide an additional heat source for the endothermic interconversion reaction. Suitable diluents can be chosen from those previously set forth in connection with the operation of the first reaction zone. Preferred diluents include steam, methane, a mixture of aromatic compounds that are by-products of the OTP reaction, and a mixture of $C_6^+$ olefins, paraffins and aromatics that are by-products of the OTP reactions performed in the first reaction and are typically recovered as an olefin-rich gasoline stream in downstream separation facilities as will be explained in conjunction with the discussion of the drawing. Of these preferred diluents, steam involves the risk of hydrothermal deactivation of the dual-function catalyst used in this second reaction zone if steam is used in high concentration but is typically used because of its ability to control and/or prevent coke formation in heaters and heat exchangers, its ready availability, its ease of separability from the products of the interconversion reaction arising in this second reaction zone and the fact that it can be used at a much lower concentration than in the first reaction zone. The amount of diluent preferably used in this second reaction zone corresponds 0.1:1 to 2.5:1 moles of diluent per mole of $C_4^+$ olefin charged to this zone and more preferably to a mole ratio of 0.25:1 to 1.5:1. Unlike the situation with respect to the first reaction zone it is to be noted that since $H_2O$ is not a by-product of the $C_4^+$ interconversion reactions performed in this second zone, there is typically no net make of diluent across this zone so that the effective amount of diluent used in this second zone is the amount charged thereto. However, it is within the scope of the present invention to charge some oxygenate to the second reaction zone in an amount sufficient to off-set the endothermic interconversion reactions arising therein.

Both the oxygenate to propylene conversion and the $C_4^+$ olefin interconversion steps are effectively carried out over a wide range of pressures including inlet total pressures between about 0.1 atm (10.1 kPa) up to about 100 atm (10.1 MPa) but it is well known that the formation of lighter olefins like propylene are favored at low pressure conditions. It is thus preferred for both of these steps to use an inlet pressure in the range of about 1 to 3 atm (101.3 to 304 kPa) and best results are achieved at about 136 to 343 kPa (5 to 35 psig).

The contact time of the reactants with the dual-function catalyst is ordinarily measured in relative terms of a Weight Hourly Space Velocity (WHSV) which is calculated for the OTP conversion step on the basis of mass hourly flow rate of the sum of the mass of oxygenate reactants passed to the first reaction zone plus the mass of any reactive hydrocarbon material present in the feedstream or any of the recycle streams passed to the first reaction zone divided by the mass of the first dual-function catalyst present in the first reaction zone. The WHSV for the $C_4^+$ olefin interconversion step is likewise calculated on the basis of mass hourly flow rate of the sum of the mass of $C_4^+$ olefin by-product stream passed thereto plus the mass of any reactive hydrocarbons present in any recycle stream or diluent stream passed thereto divided by the mass of the second dual-function catalyst present in the second reaction zone. Those skilled in the art will recognize that the contact time of the reactants with the catalyst is proportional to the inverse of the WHSV such that as the WHSV increases contact time decreases and conversely a decrease in WHSV produces an increase in contact time. WHSV for use in both the first and second reaction zones associated with the present invention can range from about 0.1 to 100 $hr^{-1}$, with a preferred range being about 0.5 to 20 $hr^{-1}$, with best results ordinarily attained in the range of 0.5 to 10 $hr^{-1}$.

In both the oxygenate to propylene conversion and the $C_4^+$ olefin interconversion steps of the present invention, it is essential to use a dual-function catalyst system having the capability of converting oxygenates to propylene as well as the capability of interconverting olefins other than propylene to propylene. Any of the catalytic materials known to the art that have the capability to catalyze these two reactions are suitable ingredients for use in the catalysts used in the present invention. The preferred dual-function catalyst contains a molecular sieve as the active ingredient and more specifically the molecular sieve has relatively small pores characterized as not larger than those associated with the 10 member pores of ZSM-5 and ZSM-11. The preferred small pore molecular sieves are defined as having pores at least a portion, preferably a major portion, of which have an average effective diameter characterized such that the adsorption capacity (as measured by the standard McBain-Bakr gravimetric adsorption method using given adsorbate molecules) shows good adsorption of oxygen and negligible adsorption of 2,3-dimethyl-butane. Negligible adsorption of a given adsorbate is adsorption of less than three percent by weight of the catalyst whereas good adsorption is an amount over this cut-off value in this test. Certain of the molecular sieves useful in the present invention have pores with an average effective diameter of less than 5 Å. The average effective diameter of the pores of preferred catalysts is determined by measurements described in D. W. Breck, ZEOLITE MOLECULAR SIEVES by John Wiley & Sons, New York (1974), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable dual-function catalysts may be chosen from among zeolitic molecular sieves and non-zeolitic molecular sieves.

Zeolitic molecular sieves in the calcined form may be represented by the general formula:

$$Me_{2/n}O:Al_2O_3:xSiO_2:yH_2O$$

where Me is a cation, x is the framework $SiO_2$ to $Al_2O_3$ ratio and has a value from about 2 to infinity, n is the cation valence and y has a value of about 2 to 100 or more and more typically about 2 to 25.

Zeolites which may be used include chabazite—also referred to as Zeolite D, clinoptilolite, erionite, ferrierite, mordenite, Zeolite A, Zeolite P, ZSM-5, ZSM-11, and MCM-22. Zeolites having a high silica content (i.e., those having framework silica to alumina ratios greater than 100 and typically greater than 150 with good results achieved at a silica to alumina mole ratio of about 150:1 to 800:1) are especially preferred. One such high silica zeolite having the structure of ZSM-5 is silicalite, as the term used herein includes both the silicapolymorph disclosed in U.S. Pat. No. 4,061,724 and also the F-silicate disclosed in U.S. Pat. No. 4,073,865, both of which are hereby incorporated by reference. The preferred zeolites for use in the dual-function catalysts used in the present invention have the structure of ZSM-5 or ZSM-11. Best results are obtained with ZSM-11 or ZSM-5 or a mixture thereof. When these preferred zeolites are used in the dual-function catalyst it is preferred that they have a silica to alumina framework mole ratio of about 20:1 to 1000:1 and more typically about 150:1 to 800:1 with best results obtained at a silica to alumina framework mole ratio of about 400:1 to 600:1.

The most preferred zeolitic dual-function catalyst for use in both conversion steps of the present invention is a zeolite having the structural configuration of ZSM-5 or ZSM-11, sometimes in the literature referred to as having a "pentasil-type" structure. A good example of this type of dual-function catalyst is disclosed in US 2003/0139635A1, the teachings of which are incorporated herein by reference. A borosilicate zeolite having the ZSM-5 or ZSM-11 structural configuration is disclosed as a particularly preferred dual-function catalyst in U.S. Pat. No. 4,433,188, the teachings of which are incorporated herein by reference. The dual-function use of a ZSM-5 catalyst system is disclosed in U.S. Pat. No. 4,579,999 wherein a methanol to olefin conversion zone is also charged with a recycle stream containing ethylene and a separate olefin-rich $C_5^+$ gasoline stream in order to increase the yield of $C_3$ to $C_4$ olefins in the first stage MTO reaction zone disclosed therein. This '999 patent contains a good disclosure of the dual-function use of a ZSM-5 catalyst system and is specifically incorporated herein by reference. The use of a zeolitic catalyst having the mordenite structural configuration is specifically disclosed in GB-A-2171718 wherein a dealuminated mordenite catalyst system having a silicon to aluminum framework atomic ratio higher than 80:1 and a sodium oxide content less than 0.1 by weight is utilized to convert a methanol-containing feedstream and a $C_4$ olefin-rich recycle stream in order to maximize the production of propylene from these materials. All of the teachings of this '718 published patent application are specifically incorporated herein by reference.

Non-zeolitic molecular sieves useful in the dual-function catalysts used in the present invention include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of aluminum and is at least 0.01, z is the mole fraction of phosphorous and is at least 0.01 and x+y+z=1. When EL is a mixture of metals, x represents the total amount of the element mixture present. Preferred elements (EL) are silicon, magnesium and cobalt with silicon being especially preferred.

The preparation of various ELAPOs are well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO); U.S. Pat. No. 4,752,651 and U.S. Pat. No. 4,310,440; all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH). These ELAPO materials are known to catalyze both the direct conversion of oxygenates to light olefins and the interconversion of olefins to a desired product olefin as can be seen from the combined teachings of U.S. Pat. No. 4,677,243 and U.S. Pat. No. 4,527,001. U.S. Pat. No. 6,455,749 has specific teachings on the use of silicoaluminophosphate catalyst (SAPO) as a dual-function catalyst and specifically has a preference for SAPO-34 as is taught in the first example contained therein. In addition the second example of this '749 patent contains a reasonably clear teaching of both the use of a SAPO-34 type of catalyst system and a ZSM-5 bound with silica type of catalyst system for use in the interconversion of $C_4$ olefins to other olefins. The teachings of the '243, '001 and '749 patents are hereby specifically incorporated by reference.

Best results with a non-zeolitic catalytic system are obtained when SAPO-34 is utilized as the principal ingredient of the dual-function catalyst. On the other hand best results with a zeolitic material are obtained with a highly siliceous ZSM-5 or ZSM-11 type of material having a silica to alumina framework mole ratio of about 20:1 to 1000:1, preferably about 150 to 800:1 and most preferably about 400:1 to 600:1. A particularly preferred embodiment involves the use of a mixture of a zeolitic catalyst system with a non-zeolitic catalyst system to form the dual-function catalyst. This mixed catalyst embodiment can be accomplished either using a physical mixture of particles containing the zeolitic material with particles containing the non-zeolitic material or the catalyst can be formulated by mixing the two types of material into a suitable binding matrix in order to form particles having both ingredients present therein. In either case the preferred combination is a mixture of ZSM-5 or ZSM-11 with SAPO-34 in relative amounts such that ZSM-5 or ZSM-11 comprises 30 to 95 wt-% of the molecular sieve portion of the mixture with a value of about 50 to 90 wt-% being especially preferred.

A preferred non-zeolitic dual-function catalyst is one in which the element (EL) content of the ELAPO varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. No. 4,440,871; U.S. Pat. No. 5,126,308, and U.S. Pat. No. 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The dual-function catalyst is preferably incorporated into porous solid particles in which the catalyst is present in an amount effective to promote the desired OTP and $C_4^+$ interconversion reactions. In one aspect, the porous solid particles comprise a catalytically effective amount of the molecular sieve catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are porous in nature and may or may not be effective to help promote the desired reactions. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieve catalyst preferably comprise about 1% to 99%, more preferably about 5% to about 90% and still more preferably about 5% to about 70%, by weight of the total composition. The preparation of solid particles comprising molecular sieve catalyst and matrix materials is conventional and well known in the art. In order to facilitate movement of the dual-function catalyst through the moving bed reactors associated with the first and second reaction zones of the present invention it is highly preferred that the particles of the catalyst be spherical or near spherical in shape. The diameter of these catalyst particles is preferably selected from the range of about 0.5 to 7 mm (0.02 to 0.28 in) with best results usually obtained with spherical particles that have a effective diameter of about 1.6 mm (0.063 in).

A particularly preferred phosphorus-modified aluminum matrix material for use in the dual-function catalysts used in the present invention is a hydrogel manufactured using the oil-drop method in accordance with the teachings of U.S. Pat. No. 4,269,717, all of the teachings of which are incorporated herein by reference. The preferred starting hydrosol is an aluminum chloride hydrosol prepared to contain aluminum anions in a weight ratio to chloride anion of about 0.7:1 to 1.5:1. In addition the molecular sieve ingredient is preferably added into the hydrosol prior to dropping to form the hydrogel according to the method discussed in the '717 patent starting at column 7, line 38. The distinction between a gel or a hydrogel and a precipitate is explained in this '717 patent in the paragraph bridging columns 2 and 3 and the gelatinous nature of the material prepared according to the teachings of the '717 patent facilitates movement of phosphorus and/or aluminum anions (i.e. makes these anions labile) and enables the hydrothermal stabilization effect that has been observed when this type of matrix material is used to make a dual-function catalyst for use in one or both of the reaction zones of the present invention.

The instant process uses two separate reaction zones containing particles of the dual-function catalyst described hereinbefore. In the case where the dual-function catalysts used in these two zones are of different compositions then the one used in the first reaction zone that performs the OTP conversion and $C_2$ olefin interconversion step is referred to as the first dual-function catalyst and the one used in the second reaction zone that perform the $C_4^+$ olefin interconversion step is called the second dual-function catalyst. In the preferred case exemplified in the drawing, the same dual-function catalyst is used to catalyze both the OTP conversion and $C_2$ olefin interconversion step and the $C_4^+$ interconversion step in separate reaction zones.

The optional selective hydrogen treatment step usable in the present invention is designed to selectively hydrogenate highly unsaturated hydrocarbons such as dienes and/or acetylenic hydrocarbons that are formed in the OTP conversion step in minor amounts (i.e. less than 2 wt-% of the amount of oxygenate feed converted and typically about 0.01 to 1 wt-% of the amount converted). While these highly unsaturated hydrocarbons do not represent a substantial source of propylene yield loss, it has been found that they are a very significant contributor to the rate of coke deposition on the preferred dual-function catalyst used in the $C_4^+$ interconversion step of the present invention. In other words they are coke-precursors and they tend to concentrate in the heavy olefin by-product streams recovered from the OTP conversion step. When one or more of these heavy olefin by-product streams are charged to the $C_4^+$ olefin interconversion step, the presence of these coke precursors therein can cause catalyst instability which in turn can lead to a significant loss in propylene selectivity. There are at least two possible sources of heavy olefin streams for use in the $C_4^+$ olefin interconversion step of the present invention. The first is a $C_4^+$ olefin-rich fraction that is separated from a vaporous fraction which in turn is derived from the effluent stream from the OTP conversion step in the primary effluent cooling and separation step. The second source is a second $C_4^+$ olefin-rich stream that is separated from the liquid hydrocarbon fraction recovered in this OTP effluent cooling and separation step. In accordance with a preferred embodiment of the present invention, at least a portion of one or both of these $C_4^+$ olefin-rich streams is charged to the optional selective hydrogen treatment step in order to selectively convert these coke precursors to the corresponding olefins. It is a preferred practice to charge at least 50 wt-% of any heavy olefin by-product stream to this hydrotreating step and more preferably 70 to 95 wt-% or more of any such stream. Since acetylene can also be present in trace amounts in the $C_2$ olefin-rich stream recovered from the OTP effluent stream for recycle to the OTP conversion step, it is within the scope of the present invention to also charge at least a portion of any $C_2$ olefin-rich fraction recovered for recycle to this optional hydrotreating step prior to recycling to the OTP conversion step with subsequent separation of the hydrotreated $C_2$ olefins for recycle to the OTP conversion step. Once again, if the amount of acetylene in this $C_2$ olefin recycle stream is too high, the preferred practice is to charge at least 50 wt-% and more preferably 70 to 95 wt-% or more of such $C_2$ olefin-rich recycle stream to the hydrotreatment step.

The optional selective hydrogen treatment step typically involves contacting at least a portion of one or more of the heavy olefin by-product streams and hydrogen with a metal-containing hydrogenation catalyst at selective hydrogenation conditions effective to convert any highly unsaturated hydrocarbons contained therein to the corresponding olefins. The catalyst is preferably maintained in the hydrotreatment zone as a fixed bed of catalyst particles which can be in any suitable shape such as spherical, cylindrical, trilobal, etc. with a spherical or cylindrical shape being preferred. These particles preferably have a diameter of about 1 to 10 mm (0.04 to 0.4 in) and/or a L/D of about 1 to 5.

The selective hydrogenation conditions utilized in this treatment step are selected from conditions known to those of skill in the art to be effective to convert highly unsaturated hydrocarbons to the corresponding olefins while minimizing or eliminating any over-hydrogenation to the corresponding fully saturated hydrocarbon. This step is typically run at a temperature of about 30° to 250° C. with best results at 75° to 150° C.; a pressure of about 1 to 40 atm or more (101 kPa to 4.05 MPa) which is sufficient to maintain a liquid phase and a liquid hourly space velocity (LHSV) of about 1 to 30 $hr^{-1}$ with best results achieved at a LHSV of about 5 to 20 $hr^{-1}$.

The amount of hydrogen charged to this treatment step is sufficient to provide 0.8 to 10 moles, preferably about 1 to 2.5 moles, of hydrogen per mole of highly unsaturated hydrocarbons charged thereto. At least a portion of the hydrogen can be dissolved in or admixed with the olefin-containing feed stream to this step or it can be added independently to the hydrotreatment zone in concurrent or countercurrent relationship to the heavy olefin-containing feed stream using technologies well-known to those skilled in this art.

The hydrogenation catalyst utilized in this optional hydrotreating step can be any of the known selective hydrogenation catalysts for this application and is preferably a combination of a catalytically effective amount of a metal hydrogenating component with a suitable porous carrier material. In some cases an olefin selectivity enhancing component (i.e. an attenuator) can be added to the catalyst in an amount sufficient to block or substantially eliminate any hydrogenation side reactions that produce a fully saturated hydrocarbon such as the corresponding paraffin hydrocarbon.

The metal hydrogenating component is preferably selected from the group of nickel, palladium, platinum and mixtures thereof with nickel being preferred. The amount used is preferably sufficient to provide a hydrogenation catalyst that contains about 0.01 to 5 wt-% metal component calculated on the metal with an amount of about 0.05 to 2 wt-% being preferred. At least a significant portion of this metal hydrogenating component is preferably maintained in the hydrogenation catalyst in a metallic state although is some cases a metallic compound may be used, such as the corresponding metallic oxide and/or sulfide, with good results.

The optional attenuation component will be selected from the group consisting of copper, silver, gold, gallium, iridium and mixtures thereof. The amount of the attenuator component added to the hydrogenation catalyst will generally be sufficient to produce about 0.01 to 2 wt-% thereof, calculated on the metal, with an amount of about 0.01 to 1 wt-% generally giving best results. When copper, silver or gold is utilized, at least a substantial portion of this optional attenuator component will typically be in the metallic state. In contrast, when gallium or iridium is used best results are obtained when a substantial portion of the attenuator component is maintained in the oxide state.

The porous carrier material for this hydrogenation catalyst can be any of the materials known to those of skill in this hydrotreating art as being suitable for their service. Suitable porous carrier material will generally have a surface area of 10 to 50 $m^2/g$ and include the following materials: 1) silica, silica gel, clays and silicates including those synthetically prepared and naturally occurring, which may or may not be acid treated, for example, attapulgus clay, china clay, diatomaceous earth, fuller's earth, kaolin, bentonite, kieselguhr, etc.; 2) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, etc.; 3) carbon and carbon-rich materials such as charcoal; 4) spinels, such as zinc aluminate, magnesium aluminate, calcium aluminate, etc.; and 5) combinations of materials from one or more of these groups. The preferred porous catalysts for use in the hydrogenation catalyst are refractory inorganic oxides, with best results obtained with an alumina material.

Suitable alumina materials are the crystalline aluminas known as gamma-, eta- and theta-alumina, with gamma- or eta-alumina giving best results. In addition, in some embodiments, the alumina carrier material may contain minor proportions of alkali and/or alkaline earth oxides and/or other well known refractory inorganic oxides such as silica, zirconia, magnesia, etc.; however, the preferred catalyst is substantially pure gamma- or eta-alumina. Preferred catalysts have an apparent bulk density of about 0.3 to about 0.9 g/cc and surface area characteristics such that the average pore diameter is about 20 to 300 Angstroms, the pore volume is about 0.1 to 1 cc/g and the surface area is about 100 to about 500 m$^2$/g. In general, best results are typically obtained with a gamma-alumina carrier material which is used in the form of spherical particles having: a relatively small diameter of about 1 to 10 mm (0.04 to 0.4 in) an apparent bulk density of about 0.3 to 0.8 g/cc, a pore volume of about 0.4 ml/g, and a surface area of about 150 to 250 m$^2$/g.

The hydrogenation catalyst can be prepared by any technique known to those skilled in the catalyst preparation art. The preferred technique involves preforming the porous carrier material and then adding the metallic component and the optional attenuator component by impregnation and/or spraying these ingredients on to the porous support either sequentially or simultaneously. Impregnation techniques that can be used include vacuum, evaporative, DIP and combinations of these techniques. It is to be noted that it is within the scope of the present invention to use a "skin" or "outer shell" impregnation technique in order to concentrate the active component on or near the perimeter of the porous support. The resulting impregnated or sprayed porous support will then be dried at a temperature of about 50° to 200° C. and typically calcined in air at a temperature of about 250° to 750° C. for a period of about 5 to 100 hours. The resulting catalyst can then be subjected to an optional reduction step typically with free hydrogen at a temperature of about 250° to 750° C. for about 1 to 10 hours.

A highly preferred feature of the present invention is the use of moving bed technology in the OTP conversion and C$_2$ olefin interconversion step and in the separate C$_4^+$ olefin interconversion step in order to enhance the selectivity of the overall process for propylene production. The use of moving bed technology in a classical MTO process is known and is shown in U.S. Pat. No. 5,157,181, all of the teachings of which are hereby incorporated by reference. This '181 patent does not however specifically address the application of this technology to the problem of maintenance of high propylene selectivity in a process for converting oxygenate to propylene, nor does the '181 patent provide any information on a two reactor zone operation or on the effect of catalyst circulation rate on the average propylene cycle yield therein. This is particularly true in the context where light and/or heavy olefin recycle is used in conjunction with a dual-function catalyst system to promote not only the oxygenate to olefin reaction but also the by-product olefin interconversion reactions discussed above. Moving bed reactors and regeneration systems suitable for use in accordance with the present invention are well known in the art and have been widely employed commercially for example in the catalytic reforming of naphtha fractions to increase octane number and to facilitate the dehydrogenation of light paraffins to make olefins.

Moving bed reaction zones for use in the instant invention can be configured in a number of ways, for example, the dual-function catalyst particles can be introduced to an upper section of the first or second reaction zone and fed by gravity through the entire volume of the reaction zone, wherein the dual-function catalyst is contacted with the feedstream or by-product stream either in a countercurrent direction to the catalyst movement or in a concurrent direction. In a preferred aspect of the present invention the feedstream or by-product stream flow is countercurrent to the catalyst flow, that is, the oxygenate feedstream or the C$_4^+$ olefin by-product feedstream is introduced into a lower portion of the reaction zone and withdrawn from an upper portion thereof. This preferred configuration can provide substantial advantages in both the OTP conversion reactions and the C$_4^+$ olefin interconversion reactions because the feedstream is thereby contacted with partially deactivated catalyst during the initial stages of the conversion when the driving force is high, and more active catalysts during the subsequent stages of the conversion when the driving force is lower.

More typically the dual-function catalyst particles are introduced into an annulus defined by concentric catalyst retaining screens that runs through the first and second reaction zones, wherein the catalyst particles travel down through the annulus and are withdrawn from a lower section of these reaction zones. The feedstream or C$_4^+$ olefin by-product stream is introduced either to the upper or lower section of the reaction zone and is passed across the annulus generally in a direction transverse to the catalyst flow. The radial bed configuration can provide low pressure drop across both the first and second reaction zones, hence good flow distribution.

During the first and second conversion zones traversal, a carbonaceous material, i.e., coke, is deposited on the catalyst as it moved downward through the reaction zones. The carbonaceous deposit material has the effect of reducing the number of active sites on the catalyst which thereby affects the extent of the overall conversion and the selectivity to propylene. During the moving bed OTP conversion and C$_2$ olefin interconversion step a portion of the coked first dual-function catalyst is thus withdrawn from the first reaction zone and regenerated in a first regeneration zone to remove at least a portion of the carbonaceous material. During the moving bed C$_4^+$ olefin by-product interconversion step a portion of the coked second dual-function catalyst is similarly withdrawn from the second reaction zone and regenerated in a second regeneration zone to remove at least a portion of the coke therefrom.

In the case where different dual-function catalysts are used in the first and second reaction, then two separate moving bed regeneration zones can be used to avoid contamination of the catalyst particles by mixing them together. A preferred embodiment is the case where two separate dual-function catalysts are used to employ UOP's common regeneration technology disclosed in U.S. Pat. No. 4,498,973 where two separate and distinct catalysts are regenerated in a single regeneration zone without commingling the catalyst particles. All of the teachings of this '973 patent are hereby incorporated by reference. In the preferred case where the same catalyst particles are used in both the first and second reaction zones then the coked particles from both zones can be mixed together and charged to a common regeneration zone. It is within the scope of the present invention in this last case to charge at least a portion of the partially coked catalyst particles withdrawn from the second reaction zone to the first reaction zone. This can be advantageous when the selectivity of the dual-function catalyst to propylene in the first reaction zone (where the OTP reaction takes place) is improved due to the partial coverage of active sites with fresh coke deposits.

In either case, the carbonaceous material is removed from the catalyst by oxidative regeneration wherein a moving bed of the catalyst particles withdrawn from the first and second reaction zones is contacted with an oxygen-containing gas stream at sufficient temperature and oxygen concentration to allow the desired amount of the carbonaceous materials to be removed by combustion from the catalyst. Depending upon the particular dual-function catalyst and conversion it can be desirable to substantially remove the deposited carbonaceous material, e.g., to less than 1 wt-% and more preferably less than 0.5 wt-%. In some cases it is advantageous to only partially regenerate the dual-function catalyst, e.g., to remove from about 30 to 80 wt-% of the carbonaceous material. Preferably, the regenerated catalyst will contain about 0 to 20 wt-% and more preferably from about 0 to 10 wt-% of the deposited carbonaceous material. It is preferred in most instances when relatively large concentrations of carbonaceous material (i.e. coke) are present on the catalyst, that is greater than about 1 wt-% carbonaceous material on the catalyst, to cause the carbon burn-off to occur with an oxygen-containing and preferably relatively dry gas stream which contains a relatively low concentration of oxygen. Preferably the oxygen content can be regulated through the use of inert gases or the recycling of flue gas materials to maintain an initial oxygen level in the gases which contact the carbonaceous material-containing catalyst of about 0.5 to 2 vol-%. By using small concentrations of oxygen, it is possible to reasonably control the oxidation of carbonaceous materials upon the dual-function catalyst without allowing excessively high temperatures to occur, thereby preventing the possibility of permanently hydrothermally damaging the molecular sieve catalyst. Temperatures used during regeneration should be in the range of about 400° to 700° C. with best results obtained at about 500° to 650° C. The details concerning the conditions for regeneration are known to those skilled in the art, for example see U.S. Pat. No. 4,873,390. The one or more regeneration zones used herein are preferably configured as a moving bed zone similar to the moving bed configuration used in the first and second reaction zones wherein the coked catalyst is fed to an upper portion of the regeneration zone and passed by gravity feed through the regeneration zone wherein at least a portion of the deposited carbonaceous material is removed and the regenerated catalyst is withdrawn from a lower section of the regeneration zone and recirculated to the first and second reaction zones.

DETAILED DESCRIPTION OF THE DRAWING

The following description of a highly preferred embodiment of the process of the present invention is made with reference to the attached drawing. In the interest of simplifying the description of the invention in order to facilitate understanding the drawing does not contain representations of heaters, heat exchangers, coolers, valves, control means and other conventional items that are well known to those of ordinary skill in the chemical engineering art except where their presence is essential to the understanding of the present invention. In this highly preferred embodiment the first and second dual-function catalysts are of the same composition and only one regeneration zone, moving bed reactor 5, is therefore necessary.

The attached drawing shows a schematic representation of an especially preferred flow scheme of the present invention in which the first reaction zone comprises three moving bed OTP reactors 1, 2 and 3, and the second reaction zone comprises one interconversion reactor 4. Reactors 1, 2 and 3 are shown in serial configuration both with respect to the oxygenate feed and to the flow of the dual-function catalyst through the reactors. Interconversion reactor 4 operates as a moving bed with a $C_4^+$ olefin feed flowing thereto via line 20, diluent via lines 13, 32 and 20 and dual-function catalyst via lines 25 and 26. The reactors themselves are shown in vertical cross section wherein the catalyst is shown flowing through an annulus which is maintained with appropriate concentric catalyst retaining screens. All three OTP reactors as well as interconversion reactor 4 operate with the charge to the reactor flowing in countercurrent relationship to the descending stream of dual-function catalyst particles. The preferred mode of operation for all three OTP reactors is to have the oxygenate feed stream flow from the outside of the OTP catalyst annulus traverse to the movement of the dual-function catalyst particles into the center portion from which the effluent stream is recovered. Reactor 4 operates in a similar manner with the $C_4^+$ by-product olefin feed stream flowing radially across the particles of the dual-function catalyst. The convention used in the drawing is that the flow of feed materials, intermediate materials and product materials is represented by solid lines and the flow of catalyst to and from the reaction zones is shown by dotted lines. The dual-function catalyst is shown as being transported by a transport medium which is preferably steam, nitrogen or any of the other inert diluents previously described. The preferred catalyst transport medium is steam due to its substantial presence in the first and second reaction zones. The details associated with the mechanical equipment necessary to engage, transport and disengage the dual-function catalyst particles as they flow from reaction zone to reaction zone and to the regeneration zone 5, are well known to those skilled in the art and need not be described further.

The dual-function catalyst utilized in reactors 1, 2, 3 and 4 comprises a ZSM-5 or ZSM-11 type of molecular sieve having a silica to alumina framework ratio of about 250:1 to 500:1 dispersed in a phosphorus-modified alumina matrix containing labile phosphorus and/or aluminum anions. It is manufactured using the "oil-drop" method disclosed in U.S. Pat. No. 4,629,717 and is utilized in a spherical form having a effective diameter of about 0.5 to 5 mm with a diameter of about 1.6 mm being especially preferred. The weight ratio of molecular sieve to phosphorus-modified alumina matrix is about 1:1 to 3:1 with a value of about 1.5:1 giving best results. The total amount of this dual-function catalyst used for conversion is preferably divided among the three OTP reactors and the one $C_4^+$ olefin interconversion reactor in equal shares with about 20 to 40% of the total amount used in reactors 1, 2, 3 and 4 filling regeneration zone 5 and the transfer lines between reactors 2 and 3 and between regeneration zone 5 and reactors 1 and 4.

The selection of the number of reactors used in the first reaction zone is based on the principle previously described of holding the conversion conditions in the individual reactors at conditions which enhance the yield of propylene. This essentially involves reactor configurations which hold the temperature differential across the individual reactors to an amount of 80° C. or less thereby avoiding a shift in the yield structure towards ethylene and simultaneously minimizing coke formation on the catalyst which accelerates rapidly as the temperature rises in the tail-end of each reactor due to the exothermic nature of the oxygenate to propylene conversion reactions. On the other hand the number of reactors necessary for the second reaction zone is based on different criteria.

Since the $C_4^+$ olefin interconversion reactions are mildly endothermic, the temperature drop across this second reaction zone must be balanced against the degree of interconversion desired and the available heat energy (i.e. enthalpy) of the $C_4^+$ olefin feed thereto as well as of the dual-function catalyst and of any diluent charged thereto. On this basis we have found that one reactor gives good results for the second reaction zone.

For purposes of startup of the flow scheme shown in the drawing, hydrocarbon recycle line 17 will be blocked off until sufficient $C_2$ olefin by-product material is obtained for initiation of recycle. Similarly water diluent recycle through lines 13, 32, 33 and 34 will be blocked off until sufficient water for recycle initiation is available. Instead an outside source of either water or steam will be injected into line 13 by means not shown just prior to the interconnection with line 9. At startup therefore, an oxygenate feedstream will flow via line 9 to the intersection with line 13 where an appropriate amount of diluent in the form of water or steam will be admixed in order to provide an oxygenate to diluent ratio of about 0.1:1 to about 12:1 with a value of about 0.5:1 to 5:1 being especially preferred for startup. The resulting mixture of oxygenate feed and diluent will then pass through appropriate feed and effluent heat exchange and heating means (not shown) in order to vaporize the resulting stream and provide a charge stream for reactor 1 that enters the reactor at a temperature of about 350° to 475° C. and a total pressure of about 136 to 343 kPa (5 to 35 psig). Sufficient dual-function catalyst will be present in reactors 1, 2, and 3 to provide a Weight Hourly Space Velocity (WHSV) of about 0.5 to 5 hr$^{-1}$ during startup with the effective WHSV increasing proportionately once recycle of $C_2$ olefinic hydrocarbon material commences. The effluent stream from reactor 1 is then withdrawn via line 10 subjected to an appropriate cooling step in order to reduce its temperature to a value close to the temperature of the charge to reactor 1 via one or more cooling means not shown, and the resulting cooled effluent stream from reactor 1 is charged to reactor 2 via line 10 and therein once again contacted with an appropriate quantity of the dual-function catalyst to convert additional amounts of oxygenate material to propylene with production of an effluent stream from reactor 2 which is withdrawn via line 11. The effluent stream from reactor 2 is once again cooled by appropriate means (not shown) to a temperature close to the inlet temperature to reactor 1 and passed via line 11 into reactor 3 where it is once again subjected to a contact with an additional amount of the dual-function catalyst under conditions which result in further conversion of unreacted oxygenate to propylene and various other by-products. Appropriate measures are taken in the design of the flow paths between reactors 1 and 2 and between 2 and 3 to minimize pressure drop across these reactors and to provide temperature differentials within these reactors which are approximately the same as that experienced in reactor 1 thereby minimizing coking of the catalyst in reactors 2 and 3 to the same degree as in reactor 1.

The effluent stream from reactor 3 is then withdrawn via line 12 and subjected to an appropriate cooling step designed to liquefy a substantial amount of the water contained therein via one or more cooling means such as a feed/effluent exchanger (not shown) and passed to a three-phase separation zone 6 in which a hydrocarbon vapor phase is formed along with a liquid hydrocarbon phase and a water phase containing minor amounts of any unreacted oxygenate that escapes from reactor 3. Since a feature of the present invention is that the activity of the dual-function catalyst in reactors 1, 2 and 3 is maintained near or at essentially start-of-cycle conditions, it is expected that the amount of unreacted oxygenate that is passed into separation zone 6 will be minimal. In other words the overall conversion achieved during the passage of the oxygenate feed through reactors 1, 2 and 3 is expected to be 97% or greater during the entire cycle.

The aqueous phase from separation zone 6 is withdrawn therefrom via line 13, a drag stream therefrom is taken via line 21 in order to dispose of surplus water and the resulting net water stream is recycled via unblocked line 13 into admixture with the oxygenate feed at the junction of lines 13 and 9. Additional quantities of water can be added to reactors 2 and 3 for cooling purposes and for partial pressure of reactants adjustment purposes via lines 13 and 34 in the case of reactor 2 and lines 13 and 33 in the case of reactor 3. Once diluent recycle is initiated the startup provisions for injection of diluent water in line 13 are terminated.

Returning to separation zone 6, the vapor phase formed therein is withdrawn via line 15 and constitutes the charge to fractionation column 7 which acts as a deethanizer and is operated to produce an ethylene-rich overhead fraction withdrawn via line 17 which also contains minor amounts of ethane and some methane and trace amounts of acetylene. A bottom fraction which essentially comprises the $C_3^+$ portion of the material charged to column 7 is withdrawn therefrom via line 16. A drag stream is withdrawn from the overhead stream in line 17 produced in column 7 via line 18 in order to control the buildup of $C_1$ and $C_2$ paraffins in the ethylene recycle loop. This drag stream may be insufficient to control methane buildup in this ethylene recycle loop and under those circumstances an additional optional treatment of this ethylene rich overhead stream is necessary in order to remove methane from this stream to the point where the methane recovery is sufficient to prevent buildup of a significant methane concentration in this ethylene recycle loop. Any suitable means for demethanizing this stream may be used in this optional step which is not portrayed in the attached drawing including the use of a demethanizer column, a methane adsorption zone, a methane-selective membrane zone, and the like methane separating means. The amount of the drag stream taken by line 18 will be about 1 to 15 vol-% of the overhead stream flowing through line 17 and more typically will comprise about 1 to 10 vol-% of this stream. The remainder of this overhead stream is then charged to reactor 1 as an ethylene-rich recycle stream in accordance with the present invention via lines 17 and 9. It is within the scope of the present invention to apportion the ethylene-rich recycle stream flowing in line 14 between the three reactors comprising the first reaction zone but we find superior results as measured by ethylene conversion when the entire amount of this ethylene stream is charged to reactor 1 via lines 17 and 9 and thereby exposed to the maximum amount of available catalyst as it flows through the three OTP reactors. In the case where acetylene content of the $C_2$ olefin-rich stream flowing in line 17 is significant it is within the scope of the present invention to divert at least a portion of this stream to an optional hydrotreatment step by means not shown for purposes of selective hydrogenation of this acetylene content to ethylene. This optional hydrotreatment step operates with a hydrogen stream and a hydrogenation catalyst in a manner previously described herein. The resulting hydrogen-treated $C_2$ olefin-rich recycle stream would then be returned to the first reaction zone by means not shown in the drawing.

The bottom stream from column 7 comprising the $C_3^+$ material charged to column 7 then flows via line 16 to depropanizer column 8 wherein this $C_3^+$ stream is subjected to fractionation conditions designed to produce a propylene-rich overhead stream, passing out of depropanizer column 8 through line 19, which is the principal product stream of the present invention and which contains minor amounts of by-product propane materials. The bottom stream from column 8 is a first stream of $C_4^+$ olefin-rich by-product material which primarily comprises $C_4$, $C_5$ and $C_6$ olefinic material along with very minor amounts of butane, pentane and $C_4$ to $C_6$ highly unsaturated hydrocarbons. All or a major portion of this bottom stream is preferably passed via line 20 to an optional selective hydrogen treatment step (not shown in the attached drawing) which contains a fixed bed of a hydrogenation catalyst comprising about 0.01 to 5 wt-% nickel on a porous alumina support. A hydrogen-rich stream is also charged to this hydrotreatment step and it contains sufficient hydrogen to provide about 0.9 to 5 moles of hydrogen per mole of highly unsaturated hydrocarbons charged to this step. The $C_4^+$ olefin-rich stream and the hydrogen stream are then contacted with the nickel-containing hydrogenation catalyst at selective hydrogenation conditions effective to convert substantially all of the highly unsaturated hydrocarbons contained in the first $C_4^+$ olefin-rich stream to the corresponding olefin. The specific condition preferably used in this optional hydrotreatment step include: inlet temperatures of about 75° to 150° C., a pressure of about 101 kPa to 405 MPa which is selected to maintain a substantially liquid stream condition and a LHSV of about 1 to 30 $hr^{-1}$. The effluent stream withdrawn from this optional step is then passed back (via means not shown in the drawing) into line 20 prior to the junction with line 35. This effluent stream is substantially free of any highly unsaturated hydrocarbons and thus has much less potential for accelerating coke formation in interconversion reactor 4.

Alternatively, if the amount of highly unsaturated hydrocarbons in this first stream of $C_4^+$ olefin-rich by-product material recovered from column 8 via line 20 is not significant enough to accelerate coke formation in reactor 4, then this stream can be passed directly to the intersection with line 35. Still another option available is to divide this first stream of $C_4^+$ olefin-rich by-product material into two portions with the first portion being passed to the optional hydrotreatment step and the second portion by-passing the optional treatment step and flowing directly to the intersection of line 20 with line 35. In this case, the ratio of the first portion to the second portion would be adjusted so that the amount of highly unsaturated hydrocarbon ultimately passed to reactor 4 via line 20 is insignificant from a coke-making standpoint.

The resulting selectively hydrogen treated $C_4^+$ olefin-rich by-product stream or the bottom stream from column 8 or a mixture of these streams is passed via line 20 to the intersection with line 35 where a drag stream is taken in an amount of about 1 to 15 vol-% and preferably about 1 to 3 vol-% in order to control buildup of paraffinic materials in this $C_4^+$ olefin recycle loop around reactor 4. The remainder of the $C_4^+$ material flowing through line 20 is then passed to the junction with line 32 where a water diluent is added thereto in an amount sufficient to provide a mole ratio of diluent to $C_4^+$ olefin of about 0.1:1 to 2.5:1. The resulting mixture of diluent and $C_4^+$ olefin is then heated by means not shown, which can include indirect heat exchange with the effluent from reactor 3, to an inlet temperature which is at least 15° C. higher than the maximum temperature reached in the first reaction zone and the resulting heated mixture is then passed into interconversion reactor 4 wherein it contacts a moving bed of the dual-function catalyst particles at $C_4^+$ olefin interconversion conditions effective to form a propylene-rich effluent stream which is withdrawn therefrom via line 24. It is to be noted that the $C_4^+$ olefin interconversion reactions occurring in reactor 4 can be performed in the substantial absence of oxygenate material except for any incidental amounts that are dissolved in the water diluent charged thereto or a minor amount of oxygenate can be charged thereto in order to off-set the endothermic interconversion reactions.

The effluent stream from interconversion reactor 4 is then withdrawn by means of line 24 and flows to the intersection with line 12 whereat it is mixed with effluent from OTP reactor 3. The resulting mixture of these two effluent streams then flows via line 12 through one or more cooling means as previously described and the resulting cooled mixture is then passed into three phase separation zone 6 which operates as previously stated.

Once the recycle streams flowing through lines 13 and 17 are up and running, then the startup mode is terminated and the full recycle mode of operation commences with the beds of the dual-function catalyst located in reactors 1, 2 and 3 functioning not only as oxygenate conversion catalyst but also as a $C_2$ olefin interconversion catalyst whereas reactor 4 is exclusively dedicated to $C_4^+$ olefin interconversion at relatively high temperatures. The sequence of events in the full recycle mode is such that a oxygenate rich feedstream enters the flow scheme via line 9 is admixed with a $C_2$ olefin recycle stream which is rich in ethylene via line 17 and then passed into the intersection with line 13 where a water or steam diluent is added in the prescribed amounts and the resulting admixture then forms the charge to reactor 1. This charge mixture flows into reactor 1 in a manner previously described after suitable heating to the specified inlet temperature.

After passage through reactor 1 and thereby traversing the bed of dual-function catalyst maintained in reactor 1 in the annular space defined by the concentric retaining screens previously described, the resulting effluent is withdrawn from reactor 1 via line 10 and flows to the intersection with line 34 wherein an additional quantity of relatively cool water diluent is admixed therewith. After suitable additional cooling to achieve the inlet temperature set forth above for reactor 1, the resulting mixture is then charged to reactor 2 wherein it makes a passage through a second annular bed of dual-function catalyst to produce an effluent stream that is withdrawn therefrom via line 11 and as is shown in the attached drawing admixed with an additional quantum of relatively cool water diluent which flows thereto via line 33. The resulting mixture is cooled by means not shown in the attached drawing to the hereinabove specified inlet temperature for reactor 1 and then flows through reactor 3 to encounter an additional quantity of dual-function catalyst with resulting production of effluent stream in line 12 which flows to the junction of line 12 with line 24 whereat it is admixed with the propylene-rich effluent stream from interconversion reactor 4. After appropriate quench and cooling, the mixture of effluent stream flows through line 12 to three-phase separation zone 6.

The amount of the dual-function catalyst utilized in OTP reactors 1, 2 and 3 and $C_4^+$ olefin interconversion reactor 4 is subject to some choice. Although a case can be made in the case of OTP reactors 1, 2 and 3 that the larger amounts of catalyst should be present in reactors 2 and 3 in order to make up for the slight amount of deactivation that will occur in reactor 1 when the catalyst flows to reactor 2 via line 28 and in reactor 3 when the catalyst flows from reactor 2 to reactor 3 via line 29, we believe that the best mode here is to run with essentially equal amounts of catalyst in the three OTP reactors or with a division which is approximately 25 to 30% of the total amount in reactors 1 and 2 with 40 to 50 vol-% of the catalyst being present in reactor 3. Similarly we believe reactor 4 should be designed to hold a similar amount of this dual-function catalyst as is maintained in reactor 1.

Reactors 1, 2, 3 and 4 are initially charged with the dual-function catalyst via lines not shown in the attached drawing that connect with lines 25, 28, 29 and 26. When the instant process is started up, catalyst circulation is commenced after the reactors are lined out at operating conditions. Catalyst circulates between the OTP reactors via catalyst lines 28 and 29 and to regeneration zone 5 via lines 30 and 27. Similarly catalyst circulates to interconversion reactor 4 via lines 25 and 26 and is withdrawn therefrom via line 27 and either passed directly to regeneration zone 5 via line 27 or passed to reactor 1 via lines 27, 31 and 25.

In regeneration zone 5, at least a portion of the coke deposits are removed from the coke-containing catalyst charged thereto via line 27 using a low severity oxidative procedure as previously explained. Also charged to regeneration zone 5 by means of line 23 is an oxygen-containing gas stream containing about 0.5 to 2 vol-% oxygen which is supplied in an amount sufficient to support combustion of a major portion of the coke charged to this zone via line 27. Regenerated catalyst is recirculated to reactor 1 via line 25, thus completing a dual-function catalyst circulation circuit defined by lines 25, 28, 29, 30 and 27. A flue gas stream is withdrawn from regeneration zone 5 via line 22.

Freshly regenerated dual-function catalyst is withdrawn from regeneration zone 5 via line 25 and a portion is charged to interconversion reactor 4 via lines 25 and 26 with the remaining portion passed back to reaction 1 via line 25. There are three distinct catalyst circulation circuits shown in the attached drawing. The first circuit as pointed out above involves circulation between reactors 1, 2 and 3 and regeneration zone 5 via lines 25, 28, 29, 30 and 27. The second circuit involves circulation between reactors 1, 2, 3 and 4 and regeneration zone 5 via lines 25, 26, 27, 28, 29, 30 and 31. The third circuit involves direct catalyst circulation between interconversion reactor 4 and regeneration zone via line 25, 26 and 27. Suitable slide valves (not shown in the attached figure) can be used at or near the intersection points of these circuits to control catalyst circulation so that the necessary amount of freshly regenerated catalyst is available to maintain activity and selectivity at desired levels for each of the reactors.

A feature of the present invention is that the flow of dual-function catalyst around these catalyst circulation circuits is selected to provide a dual-function catalyst on-stream cycle time of 700 hours or less in order to maintain catalyst activity, oxygenate conversion and propylene selectivity at or near start of cycle conditions. In other words, the flow rate of dual-function catalyst particles around these circuits is set such that a particular catalyst particle's residence time in reactors 1, 2, 3 and 4 is not more than 700 hours before it is returned to zone 5 for regeneration.

Returning to three-phase separation zone 6, it is shown in the attached drawing that the liquid hydrocarbon phase formed in this zone is withdrawn via line 14. This material generally boils in the gasoline range and can comprise a second $C_4^+$ olefin-rich recycle stream containing trace amounts of highly unsaturated hydrocarbons and a gasoline product stream of the present invention which may require further treatment due to the high content of olefinic material that is present therein. A preferred option herein is to subject this liquid hydrocarbon phase which is withdrawn from separation zone 6 via line 14 to an additional fractionation step (not shown in the drawing) in order to recover a second $C_4^+$ olefin rich overhead stream, at least a portion of which can flow directly via line 20 to interconversion reactor 4. At least a portion of this second $C_4^+$ olefin-rich can be passed to an optional selective hydrotreatment step in order to treat highly unsaturated hydrocarbons contained therein in the manner previously discussed. The resulting hydrogen-treated stream is then recycled back to interconversion reactor 4 via line 20 in order to provide a means for additional conversion of heavy olefins to propylene. A bottom stream from this optional fractionation step is recovered and it comprises the olefin-rich gasoline product stream.

What is claimed is:

1. A continuous process for selective conversion of an oxygenate feed to propylene comprising the steps of:
   a) reacting the oxygenate feed and a first diluent in an amount corresponding to about 0.1:1 to 12:1 moles of diluent per mole of oxygenate with particles of a first dual-function catalyst, having the ability to convert oxygenates to $C_3$ olefin and to interconvert $C_2$ and $C_4^+$ olefins to $C_3$ olefin, in a first reaction zone containing at least three moving bed reactors wherein the reaction zone is operated at oxygenate conversion conditions selected to convert the oxygenate to propylene and to produce a first effluent stream containing major amounts of a $C_3$ olefin product and a water by-product; lesser amounts of a $C_2$ olefin, $C_4^+$ olefins, $C_1$ to $C_4^+$ saturated hydrocarbons and aromatic hydrocarbons; and minor amounts of unreacted oxygenate, by-product oxygenates and highly unsaturated hydrocarbons;
   b) cooling and separating at least a portion of the first effluent stream in a separating zone into a vaporous fraction rich in $C_3$ olefin, a water fraction containing unreacted oxygenate and by-product oxygenates and a liquid hydrocarbon fraction containing heavier olefins, heavier saturated hydrocarbons and minor amounts of highly unsaturated hydrocarbons and aromatic hydrocarbons;
   c) passing at least a portion of the water fraction recovered in step b) to step a) to provide at least a portion of the first diluent used therein;
   d) separating the vaporous fraction into a $C_2$ olefin-rich fraction, a $C_3$ olefin-rich product fraction and a first $C_4^+$ olefin-rich fraction;
   e) charging at least a portion of the olefins contained in the $C_2$ olefin-rich fraction to step a);
   f) contacting at least a portion of the $C_4^+$ olefins contained in the first $C_4^+$ olefin-rich fraction with particles of a second dual-function catalyst, having the ability to interconvert $C_4^+$ olefins to $C_3$ olefin, in a second reaction zone containing at least one moving bed reactor wherein the second reaction zone is operated at heavy olefin interconversion conditions including an inlet temperature at least 15° C. higher than the maximum temperature used in the first reaction zone effective to convert a substantial portion of the $C_4^+$ olefin to propylene and to produce a second effluent stream containing major amounts of propylene;
   g) passing at least a portion of the second effluent stream to step b);
   h) withdrawing coke-containing particles of the first dual-function catalyst from the first reaction zone, oxidatively regenerating the withdrawn catalyst particles in a first regeneration zone and passing at least a portion of the regenerated catalyst particles back to the first reaction zone; and
   i) withdrawing coke-containing particles of the second dual-function zeolitic catalyst from the second reaction zone, oxidatively regenerating the withdrawn catalyst particles in a second regeneration zone and returning at least a portion of the regenerated catalyst particles back to the second reaction zone.

2. The continuous process as defined in claim 1 wherein the oxygenate is an oxygen-substituted aliphatic material containing 1 to 4 carbon atoms.

3. The continuous process as defined in claim 2 wherein the oxygen-substituted aliphatic material is an alcohol, an ether, an aldehyde, a ketone or a mixture thereof.

4. The continuous process as defined in claim 1 wherein the oxygenate is methanol or dimethylether (DME) or a mixture thereof.

5. The continuous process as defined in claim 1 wherein a second diluent is used in step f);

6. The continuous process as defined in claim 5 wherein the second diluent is steam.

7. The continuous process as defined in claim 1 wherein the zeolitic molecular sieve has a structure corresponding to ZSM-5 or to ZSM-11.

8. The continuous process as defined in claim 7 wherein the molecular sieve is a zeolite having a silica to alumina mole framework ratio of about 20:1 to 1000:1.

9. The continuous process as defined in claim 1 wherein the composition of the first dual-function catalyst and the second dual-function zeolitic catalyst are the same.

10. The continuous process as defined in claim 9 wherein at least a portion of the catalyst withdrawn from the second reaction zone is passed to the first reaction zone before undergoing regeneration.

11. The continuous process as defined in claim 9 wherein the regeneration substeps used in steps h) and i) are performed in one or more moving bed regeneration zones.

12. The continuous process as defined in claim 1 wherein the first and second dual-function zeolitic catalyst circulation rates through the first and the second reaction zones are set respectively to result in a catalyst on-stream cycle time of 700 hours or less.

13. The continuous process as defined in claim 1 wherein the moving bed reactors are connected in a serial flow configuration with respect to the oxygenate feed.

14. The continuous process as defined in claim 1 wherein the moving bed reactors are connected in a serial flow configuration with respect to the stream of the first dual-function zeolitic catalyst particles that passes therethrough.

15. The continuous process as defined in claim 1 wherein the liquid hydrocarbon fraction separated in step b) is further separated into a second $C_4^+$ olefin-rich fraction and a naphtha product fraction.

16. The continuous process as defined in claim 15 wherein at least a portion of the olefins contained in the first $C_4^+$ olefin-rich fraction or in the second $C_4^+$ olefin-rich fraction or in a mixture of these fractions is charged to step f).

17. The continuous process as defined in claim 15 wherein at least a portion of the first $C_4^+$ olefin-rich fraction or the second $C_4^+$ olefin-rich fraction or a mixture of these fractions is charged to a selective hydrogen treatment step and therein contacted with hydrogen in the presence of a metal containing hydrogenation catalyst at selective hydrogenation conditions effective to convert highly unsaturated hydrocarbons to the corresponding olefins thereby eliminating coke precursors and wherein at least a portion of the resulting selectively hydrotreated stream is charged to step f).

18. The continuous process as defined in claim 1 wherein the coke-containing particles of the first and second catalysts are regenerated in both cases using an oxygen-containing stream under combustion conditions selected to produce a regenerated catalyst containing less than 0.5 wt-% carbonaceous material.

19. A continuous process for selective conversion of an oxygenate feed containing methanol or a mixture of DME and methanol to propylene comprising the steps of:

a) reacting the oxygenate feed and a diluent in an amount corresponding to about 0.1:1 to 12:1 moles of diluent per mole of oxygenate with particles of a dual-function zeolitic catalyst, having the ability to convert at least a portion of the oxygenates to $C_3$ olefin and to interconvert $C_2$ and $C_4^+$ olefins to $C_3$ olefin, in a first reaction zone containing at least three moving bed reactors wherein the reaction zone is operated at oxygenate conversion conditions selected to convert the oxygenate to propylene and to produce a first effluent stream containing major amounts of a $C_3$ olefin product and a water by-product; lesser amounts of a $C_2$ olefin, $C_4^+$ olefins, $C_1$ to $C_4^+$ saturated hydrocarbons and aromatic hydrocarbons; and minor amounts of unreacted oxygenate, by-product oxygenates and highly unsaturated hydrocarbons;

b) cooling and separating at least a portion of the first effluent stream in a separating zone into a vaporous fraction rich in $C_3$ olefin, a water fraction containing unreacted oxygenate and by-product oxygenates and a liquid hydrocarbon fraction containing heavier olefins, heavier saturated hydrocarbons and minor amounts of highly unsaturated hydrocarbons and aromatic hydrocarbons;

c) passing at least a portion of the water fraction recovered in step b) to step a) or to step f) or to both step a) and step f) to provide at least a portion of the diluent used therein;

d) separating the vaporous fraction into a $C_2$ olefin-rich fraction, a $C_3$ olefin-rich product fraction and a first $C_4^+$ olefin-rich fraction;

e) charging at least a portion of the olefins contained in the $C_2$ olefin-rich fraction to step a);

f) contacting at least a portion of the $C_4^+$ olefins contained in the first $C_4^+$ olefin-rich fraction and a diluent with particles of the dual-function catalyst in a second reaction zone containing at least one moving bed reactor wherein the second reaction zone is operated at heavy olefin interconversion conditions including an inlet temperature at least 15° C. higher than the maximum temperature used in the first reaction zone effective to convert a substantial portion of the $C_4^+$ olefin to propylene and to produce a second effluent stream containing major amounts of propylene;

g) passing at least a portion of the second effluent stream to step b); and h) withdrawing coke-containing dual-function catalyst particles from the first and second reaction zones, oxidatively regenerating at least a portion of the withdrawn catalyst particles in a regeneration zone and returning at least a portion of the regenerated catalyst particles back to the first and second reaction zones.

20. The continuous process as defined in claim 19 wherein the diluent is steam.

21. The continuous process as defined in claim 19 wherein the zeolitic molecular sieve has a structure corresponding to ZSM-5 or to ZSM-11.

22. The continuous process as defined in claim 21 wherein the molecular sieve is a zeolite having a silica to alumina mole framework ratio of about 100:1 to 800:1.

23. The continuous process as defined in claim 19 wherein the dual-function zeolitic catalyst circulation rates through the first and the second reaction zones are set to result in a catalyst on-stream cycle time in each case of 700 hours or less.

24. The continuous process as defined in claim 19 wherein the liquid hydrocarbon fraction separated in step b) is further separated into a second $C_4^+$ olefin-rich fraction and a naphtha product fraction.

25. The continuous process as defined in claim 24 wherein at least a portion of the olefins contained in the first $C_4^+$ olefin-rich fraction or in the second $C_4^+$ olefin-rich fraction or in a mixture of these fractions is charged to step f).

26. The continuous process as defined in claim 24 wherein at least a portion of the first $C_4^+$ olefin-rich fraction or the second $C_4^+$ olefin-rich fraction or a mixture of these fractions is charged to a selective hydrogen treatment step and therein contacted with hydrogen in the presence of a metal containing hydrogenation catalyst at selective hydrogenation conditions effective to convert highly unsaturated hydrocarbons to the corresponding olefins thereby eliminating coke precursors and wherein at least a portion of the resulting selectively hydrotreated stream is charged to step f).

27. The continuous process as defined in claim 19 wherein the coke-containing catalyst particles are regenerated in the regeneration zone using an oxygen-containing stream under combustion conditions selected to produce a regenerated catalyst containing less than 0.5 wt-% carbonaceous material.

* * * * *

UNITED STATES PATENT AND TRADEMARK OFFICE
CERTIFICATE OF CORRECTION

PATENT NO. : 7,414,167 B2
APPLICATION NO. : 11/036312
DATED : August 19, 2008
INVENTOR(S) : Tom N. Kalnes et al.

It is certified that error appears in the above-identified patent and that said Letters Patent is hereby corrected as shown below:

Column 28
Claim 1,
Line 11, replace "dual-function catalyst" with --dual-function zeolitic catalyst--.
Line 41, replace "second dual function catalyst" with --second dual function zeolitic catalyst--.
Line 54, replace "function catalyst" with --function zeolitic catalyst--.

Column 29
Claim 9,
Line 18, replace "composition of the first dual-function catalyst" with --composition of the first dual-function zeolitic catalyst--.

Column 30
Claim 19,
Line 32, replace "particles of the dual-function catalyst" with --particles of the dual-function zeolitic catalyst--.
Line 43, replace "h) withdrawing coke-containing dual-function catalyst" with --h) withdrawing coke-containing dual-function zeolitic catalyst--.

Signed and Sealed this

Twenty-first Day of October, 2008

JON W. DUDAS
*Director of the United States Patent and Trademark Office*